US00PP14190P29

(12) United States Plant Patent
Bijl

(10) Patent No.: US PP14,190 P2
(45) Date of Patent: Sep. 30, 2003

(54) FERN PLANT NAMED 'NEVADA'

(50) Latin Name: *Nephrolepis exaltata*
Varietal Denomination: Nevada

(75) Inventor: Jacob Johannes Bijl, Burgh-Haamstede (NL)

(73) Assignee: Vitro Plus CV, Renesse (NL)

( * ) Notice: Subject to any disclaimer, the term of this patent is extended or adjusted under 35 U.S.C. 154(b) by 0 days.

(21) Appl. No.: 10/180,323

(22) Filed: Jun. 27, 2002

(51) Int. Cl.[7] ..... A01H 9/00
(52) U.S. Cl. ..... Plt./379
(58) Field of Search ..... Plt./379

*Primary Examiner*—Bruce R. Campell
*Assistant Examiner*—Michelle Kizilkaya
(74) *Attorney, Agent, or Firm*—Foley & Lardner

(57) ABSTRACT

A new and distinct Fern plant named 'NEVADA' characterized by having dark leaves, long leaves, fast growth speed and compact plant shape.

2 Drawing Sheets

Latin name of genus and species of the plant claimed: *Nephrolepis exaltata.*
Variety denomination: Nevada.

BACKGROUND OF THE INVENTION

The new cultivar originated in The Netherlands as a mutant in Renesse, The Netherlands. The parent *Nephrolepis exaltata* 'Boston Blue Bell' (unpatented). 'Nevada' was discovered and selected by the inventor, John Bijl, in a controlled environment in Renesse, The Netherlands.

Asexual reproduction of the new cultivar by tissue culture was first performed on Nov. 6, 2000 in Renesse, The Netherlands and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'NEVADA' which in combination distinguish this Fern as a new and distinct cultivar:

1. dark leaves;
2. long leaves;
3. fast growing; and
4. compact plant shape;

'NEVADA' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown in Renesse, The Netherlands under conditions which closely approximate those generally used in commercial practice.

Of the many commercial cultivars known to the present inventor, the most similar in comparison to 'NEVADA' is cultivar 'Boston Blue Bell' (unpatented). 'NEVADA' has much darker leaves than 'Blue Bell'. 'NEVADA' also has longer and wider leaves. The leaflets of 'NEVADA' are also wider and longer than the leaflets of 'Blue Bell'.

BRIEF DESCRIPTION OF THE DRAWING

The accompanying photographic drawings illustrate the overall appearance of the new Fern showing the colors as true as is reasonably possible with colored reproductions of this type.

1. Sheet one shows a 'VP002' plant on the left and to the right a comparison photo of a 'NEVADA' leaf and a 'Boston Blue Bell' leaf. The plants are 11 weeks of age.

2. Sheet two shows 'NEVADA' to the left and 'Boston Blue Bell' to the right. The plants are 11 weeks of age.

DETAILED BOTANICAL DESCRIPTION

The following observations, measurements and values describe the new cultivar as grown in Renesse, The Netherlands under conditions which closely approximate those generally used in commercial practice. 'NEVADA' is grown in a normal commercial greenhouse in temperatures ranging from 20 to 30 degrees Celsius. Maximum temperature tolerancy is 35 degrees Celsius, minimum temperature tolerancy is 10 degrees Celsius. It takes one week to iniate roots and four weeks to develop roots. Fertilizers: no particulars. In the 15 weeks after pricking the plant grows approximately 30 to 40 cm. Humidity is between 50 and 90 percent. No artificial lighting or photo periodic treatments are added. Color references are made to The Royal Horticultural Society Colour Chart (R.H.S.), edition 2001, except where general colors of ordinary significance are used. Color values were taken under daylight conditions at approximately 13.30h in Boskoop, The Netherlands. The age of the plant described is 11 weeks.

Propagation: Tissue culture.
Plant:

*Plant shape.*—Broad spreading with arching fronds.
*Height.*—Average: 23 cm.
*Width.*—Average: 57 cm.
*Growth habit.*—Fronds grow from the base of the plants.
*Growth rate.*—Moderate.
*Vigor.*—Not very vigorous.
*Growth and branching habit.*—Fronds grow from the base where short rootstocks are formed. Arching fronds grow from the nodes.

*Crop time.*—All year (greenhouse grown).
*Winter hardiness/weather tolerance.*—USDA Zone 10.
Rooting time:
*Rooting habit.*—Freely branching.
*Time to initiate roots.*—1 week.
*Time to develop roots.*—4 weeks.
Frond description:
*Leaf arrangement.*—Fronds crowded (alternate) on the rhizome (rootstock).
*Length.*—Average: 29 cm.
*Width.*—Average: 6.2 cm.
*Rachis diameter.*—Average: 1 mm.
*Rachis color.*—Upper side: green; RHS-CC 141A, underside green; RHS-CC 143A. Rachis with only very little greenish- to silvery-white hairs, these hairs have an average length of approximately 2 mm.
Pinnae description:
*Quantity of pinnae per frond.*—Average: 52 (varies from 42 to 62).
*Shape.*—Narrow ovate to narrow triangular.
*Length.*—Average: 2.9 cm.
*Width.*—Average: 1 cm.
*Apex.*—Obtuse.
*Base.*—Truncate.
Aspect: Pinnae are thin and smooth on both sides.
*Attachment.*—Pinnae attached by vein only.
*Margin.*—Finely crenate (crenulate).
*Texture.*—Smooth.
*Color of upper surface.*—Mature leaf: Green; RHS-CC 137A, but slightly more yellowish. Immature leaf: Green; RHS-CC 143A.
*Color of lower surface.*—Mature leaf: Green; RHS-CC 137A. Immature leaf: Green; RHS-CC 143A/B.
Flowers:
*State if none observed.*—None observed.
*Seeds.*—None observed.
Disease resistance: Not more susceptible to pests and diseases than similar varieties.

I claim:

1. A new and distinct Fern plant named 'NEVADA', substantially as illustrated and described herein.

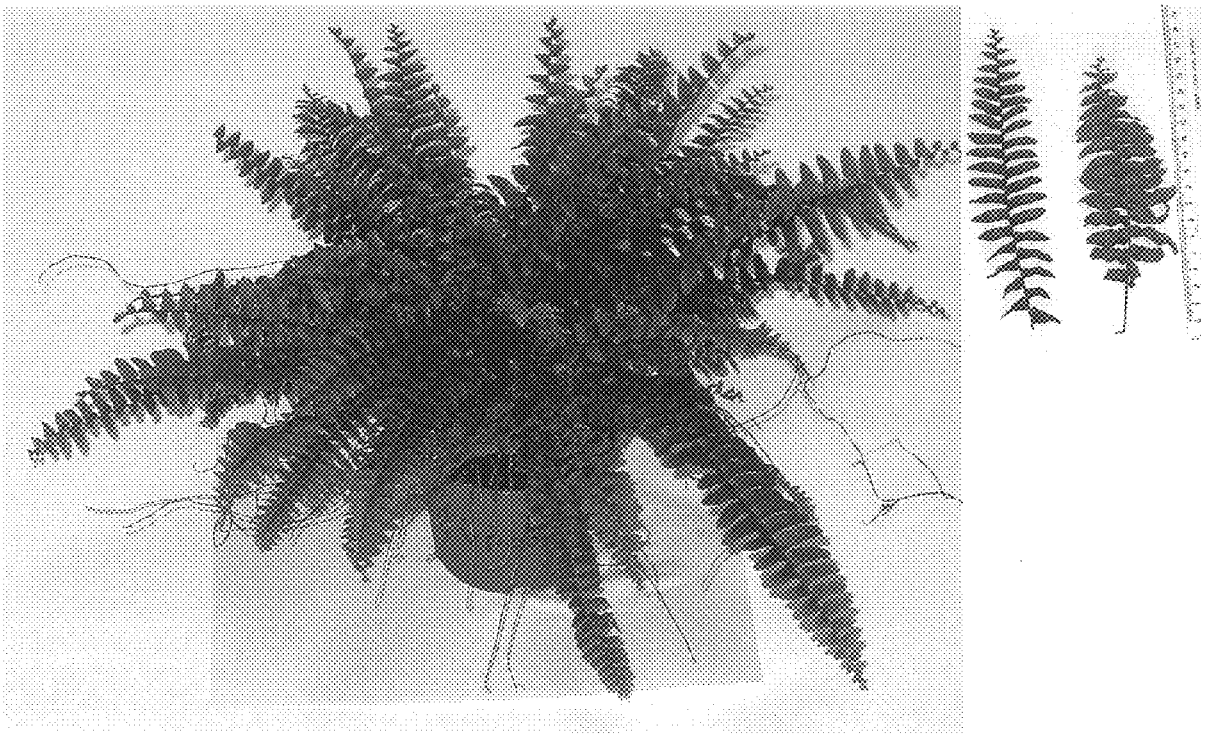

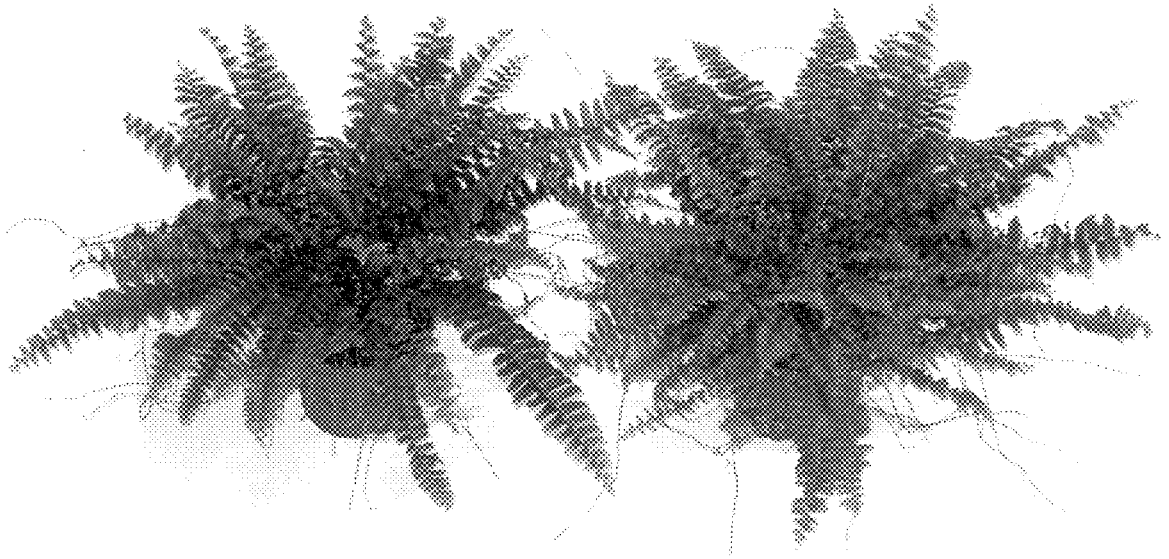

* * * * *